United States Patent [19]

Oh-Kita et al.

[11] Patent Number: 4,803,302
[45] Date of Patent: Feb. 7, 1989

[54] PROCESS FOR THE PRODUCTION OF METHACRYLIC ACID

[75] Inventors: Motomu Oh-Kita; Masaaki Kato; Masao Kobayashi, all of Ohtake, Japan

[73] Assignee: Mitsubishi Rayon Co., Ltd., Tokyo, Japan

[21] Appl. No.: 103,580

[22] PCT Filed: Jan. 6, 1987

[86] PCT No.: PCT/JP87/00008
   § 371 Date: Aug. 21, 1987
   § 102(e) Date: Aug. 21, 1987

[87] PCT Pub. No.: WO87/04086
   PCT Pub. Date: Jul. 16, 1987

[30] Foreign Application Priority Data

Jan. 8, 1986 [JP] Japan .................................. 61-1684
   Jan. 9, 1986 [JP] Japan .................................. 61-2632

[51] Int. Cl.⁴ .................... C07C 51/25; C07C 57/055
[52] U.S. Cl. .................................. 562/534; 502/206; 502/209
[58] Field of Search .............. 562/534; 502/206, 209

[56] References Cited

U.S. PATENT DOCUMENTS

4,320,227 3/1982 Matsumoto et al. ............. 562/534
   4,341,900 7/1982 Ishii et al. ....................... 562/532
   4,558,029 12/1985 Paparizos et al. ................ 502/211

FOREIGN PATENT DOCUMENTS

0046333 2/1982 European Pat. Off. .
   0051348 5/1982 European Pat. Off. .
   0124706 11/1984 European Pat. Off. .
   2704991 8/1977 Fed. Rep. of Germany .
   3308625 9/1984 Fed. Rep. of Germany .
   210043 11/1984 Japan .................................. 562/534

*Primary Examiner*—Vivian Garner
*Attorney, Agent, or Firm*—Armstrong, Nikaido, Marmelstein & Kubovcik

[57] ABSTRACT

A catalyst represented by the general formula

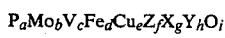

$$P_a Mo_b V_c Fe_d Cu_e Z_f X_g Y_h O_i$$

wherein X represents at least one or more of the elements selected form the group consisting of potassium, rubidium, cesium and thallium, Y represents at least one or more of the elements selected from the group consisting of tellurium, lanthanum, boron, silver, chromium, magnesium and barium, Z represents any one of the elements of zirconium or antimony, a to i denote atomic ratios of respective elements, and when $b=12$, $a=0.3-4$, $c=0.01-3$, $d=0.01-4$, $e=0.01-3$, $f=0.01-3$, $g=0.01-3$, $h=0.001-5$ and i denotes the number of oxygen atoms required for satisfying the valence number of the said ingredients, and a process for the production of methacrylic acid comprising contacting methacrolein in vapor phase in the presence of said catalyst.

7 Claims, No Drawings

PROCESS FOR THE PRODUCTION OF METHACRYLIC ACID

TECHNICAL FIELD

This invention relates to a process for the production of methacrylic acid by vapor phase catalytic oxidation of methacrolein and a catalyst to be used for the process.

BACKGROUND ART

There have hitherto been disclosed in patents enormous methods with reference to processes for producing unsaturated carboxylic acids by vapor phase catalytic oxidation of unsaturated aldehydes, for example, a process for the production of methacrylic acid by vapor phase catalytic oxidation of methacrolein. These patents put emphasis on the method of producing acrylic acid from acrolein, and the method was impractical because of a low rate of selectivity due to severe side reaction and short life of the catalysts disclosed in the patents on using the catalysts as the ones for producing methacrylic acid.

On the other hand, many catalysts have been proposed for producing methacrylic acid from methacrolein. But these catalysts have problems that they are insufficient in reactivity, catalyst activity decreases greatly with the passage of time or high temperature is required for the reaction, so that a further improvement for the use as an industrial catalyst is required.

DISCLOSURE OF THE INVENTION

The object of this invention is to provide a process for producing advantageously methacrylic acid from methacrolein. In particular, the object of this invention is to provide a catalyst which is excellent in activity, selectivity and life and thus has high practicability for producing methacrylic acid and a process for producing methacrylic acid by using said catalyst.

BEST MODE FOR PRACTICING THE INVENTION

This invention relates to a catalyst practicable for producing methacrylic acid by the vapor phase oxidation of methacrolein with molecular oxygen, which is represented by the general formula

$P_a Mo_b V_c Fe_d Cu_e Z_f X_g Y_h O_i$ wherein X represents at least one or more of the elements selected from the group consisting of potassium, rubidium, cesium and thallium, Y represents at least one or more of the elements selected from the group consisting of tellurium, lanthanum, boron, silver, chromium, magnesium and barium, Z represents any one of the elements of zirconium or antimony, a to i denote atomic ratios of respective elements, and when $b=12$, $a=0.3-4$, $c=0.01-3$, $d=0.01-4$, $e=0.01-3$, $f=0.1-3$, $g=0.1-3$, $h=0.001-5$ and i denotes the number of oxygen required for satisfying the valence number of the aforementioned ingredients, and a process for producing methacrylic acid characterized by using said catalyst.

The catalyst of this invention has a basic composition of phosphorus, molybdenum, vanadium and copper, and comprises additionally at least one or more of the elements selected from the group consisting of a specific amount of iron and zirconium or antimony and potassium, rubidium, cesium and thallium, and at least one or more of specific elements selected from the group consisting of tellurium, lanthanum, boron, silver, chromium, magnesium and barium. The catalyst may be used industrially very advantageously and thus the catalyst activity can be maintained at a high level over a long period of time, because the catalyst is high in activity and selectivity for producing methacrylic acid from methacrolein and it can provide a sufficient rate of reaction even at low reaction temperature owing to its high activity. The atomic ratios of respective elements may be any one of the aforementioned ratios and may be suitably selected from the aforementioned ranges of the ratios. The ratios are preferably in the ranges 1-2.5 for a, 0.05-1.5 for c, 0.5-2 for d, 0.05-2 for e, 0.1-1.5 for f, 0.1-2 for g and 0.01-2 for h when b is 12.

As the process for preparing the catalyst of this invention, a variety of methods such as evaporation to dryness, precipitation and the like may be used provided that the components will not distribute unevenly departing from the aforementioned atomic ranges.

As the raw materials used for preparing the catalyst, there may be used nitrates, carbonates, ammonium salts, halides, oxides or the like of respective elements in combinations thereof.

The catalyst of this invention may be used as a bare catalyst or carried or diluted with such known inert carriers such as silica, alumina, silica-alumina, silicon carbide or the like.

The catalyst of this invention can be used for producing acrylic acid from acrolein by controlling the reaction conditions.

According to the process for producing methacrylic acid by using the aforementioned catalyst as another aspect of this invention, it is possible to obtain methacrylic acid from methacrolein in high yield and high selectivity and to maintain the catalyst activity over a long period of time, so that the process of this invention has great industrial advantages.

On the practice of the process according to this invention, the concentration of methacrolein in the raw material gases may be varied over a wide range. However, it is preferably in the range of 1-20% by volume, particularly 3-10%.

Methacrolein as the raw material may contain a small amount of impurities such as lower aldehydes or the like, and these impurities will not affect substantially the reaction.

It is economical to use air as an oxygen source, and it is also possible to use air enriched with pure oxygen, if necessary.

The content of oxygen in the feed gas is defined by a mole ratio to methacrolein and preferably is in the range of 0.3-4, particularly in the range of 0.4-2.5.

The raw material gases may be diluted by mixing with inert gases such as nitrogen, steam, carbon dioxide or the like. The reaction is preferably carried out in the pressure range from normal pressure to several atmospheric pressures. The reaction temperature can be selected from the range of 230°-450° C., particularly preferably 250°-400° C. The reaction may be carried out either in a fixed bed or in a fluidized bed.

The process for preparing the catalyst of this invention and the preparation examples with the catalyst thus prepared are specifically explained below.

In the Examples and Comparative Examples, "part" means part by weight, and analysis was carried out by gas chromatography. The conversion of methacrolein and the selectivity for methacrylic acid will be defined as follows.

Conversion of methacrolein (%) =

$$\frac{\text{moles of methacrolein reacted}}{\text{moles of methacrolein fed}} \times 100$$

Selectivity for methacrylic acid (%) =

$$\frac{\text{moles of methacrylic acid produced}}{\text{moles of methacrolein reacted}} \times 100$$

EXAMPLE 1

One hundred parts of ammonium paramolybdate, 1.7 parts of ammonium metavanadate and 4.8 parts of potassium nitrate were dissolved in 300 parts of pure water. To this mixture was added a solution of 8.2 parts of 85% phosphoric acid in 10 parts of pure water. Then, a solution of 1.1 parts of telluric acid in 10 parts of pure water was further added, and the temperature of the mixture was raised with stirring up to 95° C.

Next, a solution of 2.3 parts of copper nitrate, 3.8 parts of ferric nitrate and 2.5 parts of zirconyl nitrate in 40 parts of pure water was added, and the mixture was heated with stirring up to a temperature of 100° C. and evaporated to dryness.

The solid obtained was dried at 130° C. for 16 hours and subjected to pressure molding and then to thermal treatment at 380° C. for 5 hours under a stream of air, whereupon the solid was used as a catalyst.

The catalyst thus obtained had a composition of elements other than oxygen (referred to as composition hereinafter)

$P_{1.5}Mo_{12}V_{0.3}Fe_{0.2}Cu_{0.2}Zr_{0.2}K_1Te_{0.1}$.

The catalyst was charged in a reactor and a mixed gas comprising 5% of methacrolein, 10% of oxygen, 30% of steam and 55% of nitrogen (by volume) was flown at a reaction temperature of 290° C. for a contact time of 3.6 seconds. Products were collected and upon gas chromatographical analysis the conversion of methacrolein was 87.0% and the selectivity for methacrylic acid was 86.2%.

When the reaction was continued for about 1000 hours under the same conditions, the conversion of methacrolein was 86.8% and the selectivity for methacrylic acid was 86.3%.

EXAMPLE 2

In accordance with Example 1, a catalyst having a composition of $P_{1.5}Mo_{12}V_{0.5}Fe_{0.4}Cu_{0.3}Zr_{0.1}K_{0.5}Rb_{0.6}B_{0.2}$ was prepared and reaction was carried out under the same conditions as in Example 1. The conversion of methacrolein was 86.8% and the selectivity for methacrylic acid was 86.1%.

EXAMPLE 3

One hundred parts of ammonium paramolybdate, 1.7 parts of ammonium metavanadate and 9.2 parts of cesium nitrate were dissolved in 300 parts of pure water.

A solution of 5.4 parts of 85% phosphoric acid in 10 parts of pure water was added to the mixture, and the temperature of the whole mixture was raised with stirring up to 95° C. Next, a solution of 1.1 parts of copper nitrate, 5.7 parts of ferric nitrate, 3.8 parts of zirconyl nitrate and 0.4 parts of silver nitrate in 60 parts of pure water was added, and the mixture was heated with stirring up to a temperature of 100° C. and evaporated to dryness. The solid obtained was dried at 130° C. for 16 hours and subjected to pressure molding and then to thermal treatment at 380° C. for 5 hours under a stream of air, whereupon the solid was used as a catalyst.

The catalyst thus obtained had a composition of elements $P_1Mo_{12}V_{0.3}Fe_{0.3}Cu_{0.1}Zr_{0.3}Cs_1Ag_{0.05}$.

Using the catalyst, reaction was carried out under the same conditions as in Example 1. The conversion of methacrolein was 88.1% and the selectivity for methacrylic acid was 84.9%.

EXAMPLES 4–6

In accordance with Example 3, catalysts shown in Table 1 were prepared, and the reaction was carried out in the same manner as in Example 1 to obtain the results listed in Table 1.

TABLE 1

| Example | Composition of catalyst (by atomic ratios) | Conversion of methacrolein (%) | Selectivity for methacrylic acid (%) |
|---|---|---|---|
| 4 | $P_2Mo_{12}V_{0.5}Fe_{0.3}Cu_{0.1}Zr_{0.3}Tl_{0.8}Cr_{0.2}$ | 87.3 | 85.7 |
| 5 | $P_{1.5}Mo_{12}V_{0.5}Fe_{0.3}Cu_{0.2}Zr_{0.2}Tl_{0.8}Mg_{0.5}$ | 86.0 | 87.1 |
| 6 | $P_{1.5}Mo_{12}V_{0.5}Fe_{0.5}Cu_{0.1}Zr_{0.5}Cs_1Ba_{0.3}La_{0.1}$ | 86.3 | 86.6 |

EXAMPLE 7

One hundred parts of ammonium paramolybdate, 5.5 parts of ammonium metavanadate and 4.8 parts of potassium nitrate were dissolved in 300 parts of pure water. To this mixture was added a solution of 9.8 parts of 85% phosphoric acid in 15 parts of pure water. Then a solution of 1.1 parts of telluric acid in 10 parts of pure water and 0.6 part of boric acid were further added, and the temperature of the mixture was raised with stirring up to 95° C.

Next, a solution of 3.4 parts of copper nitrate, 7.6 parts of ferric nitrate, 6.3 parts of zirconyl nitrate and 1.2 parts of barium nitrate in 80 parts of pure water was added, and the mixture was heated with stirring up to a temperature of 100° C. and evaporated to dryness. The solid obtained was dried at 130° C. for 16 hours and subjected to pressure molding and then to thermal treatment at 380° C. for 5 hours under a stream of air, whereupon the solid was used as a catalyst.

The catalyst thus obtained had a composition of elements $P_{1.8}Mo_{12}V_1Fe_{0.4}Cu_{0.3}Zr_{0.5}K_1Te_{0.1}B_{0.2}Ba_{0.1}$.

Using the catalyst, reaction was carried out under the same conditions as in Example 1. The conversion of methacrolein was 86.7% and the selectivity for methacrylic acid was 86.5%.

EXAMPLES 8-12

In accordance with Example 7, catalysts shown in Table 2 were prepared, and reaction was carried out in the same manner as Example 1 to obtain the results listed in Table 2.

TABLE 2

| Example | Composition of catalyst (by atomic ratios) | Conversion of methacrolein (%) | Selectivity for methacrylic acid (%) |
|---|---|---|---|
| 8 | $P_{1.5}Mo_{12}V_{0.5}Fe_{0.2}Cu_{0.1}Zr_{0.1}K_1B_{0.3}Cr_{0.05}$ | 87.1 | 85.9 |
| 9 | $P_{1.4}Mo_{12}V_{0.5}Fe_{0.3}Cu_{0.2}Zr_{0.1}K_1B_{0.3}Mg_{0.05}$ | 87.3 | 85.6 |
| 10 | $P_{1.4}Mo_{12}V_{0.5}Fe_{0.4}Cu_{0.2}Zr_{0.1}K_1B_{0.3}Cr_{0.05}Mg_{0.05}Ba_{0.05}$ | 86.9 | 86.2 |
| 11 | $P_{1.5}Mo_{12}V_{0.7}Fe_{0.4}Cu_{0.1}Zr_{0.05}Rb_1La_{0.5}$ | 86.9 | 86.0 |
| 12 | $P_{1.7}Mo_{12}V_{0.5}Fe_{0.4}Cu_{0.1}Zr_{0.1}K_1Ba_{0.05}$ | 87.3 | 85.5 |

EXAMPLE 13

Using the catalyst prepared in Example 1, reaction was carried out under the same conditions as in Example 1 except that the reaction temperature was changed to 305° C. The conversion of methacrolein was 97.0% and the selectivity for methacrylic acid was 80.8%.

EXAMPLE 14

Using the catalyst prepared in Example 2, reaction was carried out under the same conditions as in Example 1 except that the reaction temperature was changed to 305° C. The conversion of methacrolein was 96.8% and the selectivity for methacrylic acid was 80.8%.

EXAMPLE 15

Using the catalyst prepared in Example 3, reaction was carried out under the same conditions as in Example 1 except that the reaction temperature was changed to 305° C. The conversion of methacrolein was 97.3% and the selectivity for methacrylic acid was 80.6%.

COMPARATIVE EXAMPLES 1-3

In accordance with Example 1, catalysts shown in Table 3 were prepared, and reaction was carried out under the same conditions as in Example 1 to obtain the results listed in Table 3.

TABLE 3

| Comparative Example | Composition of catalyst (by atomic ratios) | Conversion of methacrolein (%) | Selectivity for methacrylic acid (%) |
|---|---|---|---|
| 1 | $P_{1.5}Mo_{12}V_{0.3}Cu_{0.2}K_1$ | 82.3 | 81.4 |
| 2 | $P_{1.5}Mo_{12}V_{0.3}Cu_{0.2}Fe_{0.2}K_1$ | 84.0 | 83.9 |
| 3 | $P_{1.5}Mo_{12}V_{0.3}Cu_{0.2}Zr_{0.2}K_1$ | 85.4 | 84.3 |

EXAMPLE 16

One hundred parts of ammonium paramolybdate, 2.8 parts of ammonium metavanadate and 4.8 parts of potassium nitrate were dissolved in 300 parts of pure water. To this mixture was added a solution of 8.2 parts of 85% phosphoric acid in 10 parts of pure water. Then, a solution of 3.3 parts of telluric acid in 20 parts of pure water and 3.4 parts of antimony trioxide were further added, and the temperature of the mixture was raised with stirring up to 95° C.

Next, a solution of 3.4 parts of copper nitrate and 5.7 parts of ferric nitrate in 30 parts of pure water was added, and the mixture was heated with stirring up to a temperature of 100° C. and evaporated to dryness.

The solid obtained was dried at 130° C. for 16 hours and subjected to pressure molding and then to thermal treatment at 380° C. for 5 hours under a stream of air, whereupon the solid was used as a catalyst.

The catalyst thus obtained had a composition of elements $P_{1.5}Mo_{12}V_{0.5}Fe_{0.3}Cu_{0.3}Sb_{0.5}K_1Te_{0.3}$.

The catalyst was charged in a reactor and a mixed gas comprising 5% of methacrolein, 10% of oxygen, 30% of steam and 55% of nitrogen (by volume) was flown at a reaction temperature of 290° C. for a contact time of 3.6 seconds. Products were collected and upon gas chromatographical analysis conversion of methacrolein was 87.5% and the selectivity for methacrylic acid was 87.3%.

When the reaction was continued for about 1000 hours under the same conditions, the conversion of methacrolein was 87.3% and the selectivity for methacrylic acid was 87.0%.

EXAMPLE 17

In accordance with Example 16, a catalyst having a composition of $P_1Mo_{12}V_1Fe_{0.2}Cu_{0.1}Sb_1Cs_1B_{0.3}$ was prepared, and reaction was carried out under the same conditions as in Example 16. The conversion of methacrolein was 86.5% and the selectivity for methacrylic acid was 87.9%.

EXAMPLE 18

One hundred parts of ammonium paramolybdate, 2.8 parts of ammonium metavanadate and 4.8 parts of potassium nitrate were dissolved in 300 parts of pure water.

To this mixture was added a solution of 5.4 parts of 85% phosphoric acid in 10 parts of pure water. Then, 4.8 parts of antimony trioxide was further added to the mixture, and the temperature was raised with stirring up to 95° C.

Next, a solution of 1.1 parts of copper nitrate, 9.5 parts of ferric nitrate and 0.4 part of silver nitrate in 40 parts of pure water was added, and the mixture was heated with stirring up to 100° C. and evaporated to dryness.

The solid obtained was dried at 130° C. for 16 hours and subjected to pressure molding and then to thermal treatment at 380° C. for 5 hours under a stream of air, whereupon the solid was used as a catalyst.

The catalyst thus obtained had a composition of elements $P_1Mo_{12}V_{0.5}Fe_{0.5}Cu_{0.1}Sb_{0.7}K_1Ag_{0.05}$.

Using the catalyst, reaction was carried out under the same conditions as in Example 16. The conversion of methacrolein was 88.0% and the selectivity for methacrylic acid was 86.7%.

EXAMPLES 19-26

In accordance with Example 18, catalysts shown in the following Table were prepared. Reaction was carried out under the same conditions as in Example 16, and the results shown in Table 4 were obtained.

TABLE 4

| Example | Compostion of catalyst (by atomic ratios) | Conversion of methacrolein (%) | Selectivity for methacrylic acid (%) |
|---|---|---|---|
| 19 | $P_{1.5}Mo_{12}V_{0.5}Fe_{0.3}Cu_{0.5}Sb_{0.5}Rb_1Mg_{0.3}$ | 87.2 | 87.3 |
| 20 | $P_{1.5}Mo_{12}V_1Fe_{0.3}Cu_{0.1}Sb_1K_{0.3}Cs_{0.6}La_{0.2}Ag_{0.1}$ | 87.9 | 86.9 |
| 21 | $P_2Mo_{12}V_{0.5}Fe_{0.3}Cu_{0.2}Sb_{0.5}Tl_{0.8}Ba_{0.3}$ | 86.8 | 87.7 |
| 22 | $P_{1.9}Mo_{12}V_{0.5}Fe_{0.4}Cu_{0.2}Sb_1K_1Ag_{0.05}Mg_{0.1}$ | 87.0 | 87.4 |
| 23 | $P_{1.5}Mo_{12}V_{0.8}Fe_{0.4}Cu_{0.2}Sb_1Tl_{0.8}B_{0.3}Mg_{0.05}$ | 88.1 | 86.6 |
| 24 | $P_{1.5}Mo_{12}V_{0.5}Fe_{0.3}Cu_{0.1}Sb_{0.8}K_1Ag_{0.05}Mg_{0.1}Ba_{0.1}$ | 87.4 | 87.1 |
| 25 | $P_{1.5}Mo_{12}V_{0.7}Fe_{0.2}Cu_{0.1}Sb_1K_1B_{0.4}Ag_{0.05}Mg_{0.1}$ | 87.8 | 87.0 |
| 26 | $P_{1.5}Mo_{12}V_{0.5}Fe_{0.3}Cu_{0.2}Sb_{0.5}K_{0.5}Tl_{0.3}Mg_{0.1}Ba_{0.1}$ | 88.0 | 86.4 |

EXAMPLE 27

In accordance with Example 18, a catalyst having a composition represented by $P_{1.7}Mo_{12}V_{0.7}Fe_{0.4}Cu_{0.1}Sb_{0.9}K_1La_{0.05}$ was prepared, and reaction was carried out under the same conditions as in Example 16. The conversion of methacrolein was 87.6% and the selectivity for methacrylic acid was 87.0%.

EXAMPLE 28

Using the catalyst prepared in Example 16, reaction was carried out under the same conditions as in Example 16 except that the reaction temperature was changed to 305° C. The conversion of methacrolein was 97.3% and the selectivity for methacrylic acid was 81.5%.

EXAMPLE 29

Using the catalyst prepared in Example 17, reaction was carried out under the same conditions as in Example 16 except that the reaction temperature was changed to 305° C. The conversion of methacrolein was 97.3% and the selectivity for methacrylic acid was 81.2%.

EXAMPLE 30

Using the catalyst prepared in Example 18, reaction was carried out under the same conditions as in Example 16 except that the reaction temperature was changed to 305° C. The conversion of methacrolein was 97.9% and the selectivity for methacrylic acid was 80.8%.

COMPARATIVE EXAMPLES 4-6

In accordance with Example 16, comparative catalysts shown in Table 5 were prepared, and reaction was carried out under the same conditions as in Example 16 to obtain the results listed in Table 5.

TABLE 5

| Comparative Example | Composition of catalyst (by atomic ratios) | Conversion of methacrolein (%) | Selectivity for methacrylic acid (%) |
|---|---|---|---|
| 4 | $P_{1.5}Mo_{12}V_{0.5}Cu_{0.3}K_1$ | 82.0 | 82.0 |
| 5 | $P_{1.5}Mo_{12}V_{0.5}Cu_{0.3}Fe_{0.3}K_1$ | 84.2 | 83.1 |
| 6 | $P_{1.5}Mo_{12}V_{0.5}Cu_{0.3}Sb_{0.5}K_1$ | 83.1 | 82.9 |

We claim:

1. A process for the production of methacrylic acid by the vapor phase catalytic oxidation of methacrolein with molecular oxygen comprising contacting a raw material gas containing methacrolein and molecular oxygen with a catalyst represented by the formula

$$P_aMo_bV_cFe_dCu_eZ_fX_gY_hO_i$$

wherein X represents at least one of the elements selected from the group consisting of potassium, rubidium, cesium and thallium, Y represents at least one of the elements selected from the group consisting of tellurium, lanthanum, boron, silver, chromium, magnesium and barium, Z represents any one of the elements of zirconium or antimony, a to i denote atomic ratios of the respective elements and b=12, a=0.3-4, c=0.01-3, d=0.1-4, e=0.01-3, f=0.01-3, g=0.01—3, h=0.001-5 and i denotes the number of oxygen atoms required for satisfying the valence number of said elements.

2. A process for the production of methacrylic acid according to claim 1, wherein Z in the formula of said catalyst is zirconium.

3. A process for the production of methacrylic acid according to claim 1, wherein Z in the formula of said catalyst is antimony.

4. A process for the production of methacrylic acid according to claim 1, wherein the concentration of methacrolein contained in said raw material gas is in the range of 1-20% by volume.

5. A process for the production of methacrylic acid according to claim 1, wherein the molar ratio of molecular oxygen contained in said raw material to methacrolein is in the range of 0.3-4.

6. A process for the production of methacrylic acid according to claim 1, wherein said raw material gas is diluted with an inert gas selected from nitrogen, steam and carbon dioxide gas.

7. A process for the production of methacrylic acid according to any one of claims 1-6, wherein said vapor phase oxidation is carried out at a temperature selected from the range of 230°-450° C. under pressure.

* * * * *